United States Patent [19]
Grootenhuis et al.

[11] Patent Number: 6,034,067
[45] Date of Patent: Mar. 7, 2000

[54] SERINE PROTEASE INHIBITORS

[75] Inventors: Peter Diederik Jan Grootenhuis, Oss; Adrianus Petrus Antonius de Man, Loon Op Zand; Anton Egbert Peter Adang, Eindhoven, all of Netherlands

[73] Assignee: Akzo Nobel, N.V., Arnhem, Netherlands

[21] Appl. No.: 09/125,169

[22] PCT Filed: Feb. 11, 1997

[86] PCT No.: PCT/EP97/00625

§ 371 Date: Aug. 12, 1998

§ 102(e) Date: Aug. 12, 1998

[87] PCT Pub. No.: WO97/30073

PCT Pub. Date: Aug. 21, 1997

[30] Foreign Application Priority Data

Feb. 13, 1996 [EP] European Pat. Off. .............. 96200334
Feb. 19, 1996 [EP] European Pat. Off. .............. 96200421
Aug. 23, 1996 [EP] European Pat. Off. .............. 96202337

[51] Int. Cl.[7] .......................... A61K 38/05; A61K 38/06; A61K 38/07; C07K 5/02; C07K 5/06

[52] U.S. Cl. .............................. 514/18; 514/20; 514/212; 514/269; 514/315; 514/349; 514/424; 514/563; 530/330; 530/331; 540/527; 544/319; 546/242; 546/297; 548/543; 548/549; 562/433; 562/442; 562/560; 564/86; 564/95; 564/153; 564/157; 564/159

[58] Field of Search ..................... 530/331, 330; 514/20, 212, 269, 315, 349, 424, 563, 601, 604, 605, 619, 626, 18; 540/527; 544/319; 546/242, 297; 548/543, 550; 562/433, 442, 560; 564/86, 88, 95, 153, 157, 159

[56] References Cited

FOREIGN PATENT DOCUMENTS

| | | |
|---|---|---|
| 0408371 | 1/1991 | European Pat. Off. . |
| 0672658 | 9/1995 | European Pat. Off. . |
| 0686642 | 12/1995 | European Pat. Off. . |
| WO 9425051 | 11/1994 | WIPO . |
| WO 9429336 | 12/1994 | WIPO . |
| WO 9523608 | 9/1995 | WIPO . |
| WO 9535311 | 12/1995 | WIPO . |
| WO 9619483 | 6/1996 | WIPO . |
| WO 9731937 | 9/1997 | WIPO . |

OTHER PUBLICATIONS

Database WPI, Week 9613, XP002031054, Jan. 23, 1996.

Costanzo et al., *Journal of Medicinal Chemistry,* 39:16:3039–3043, 1996.

Jones et al., *Letters in Peptide Science,* 2:147–154, 1995.

Krug et al., *Chemical Abstracts,* 80:25:477, Abs. 146496q, 1974.

*Primary Examiner*—Jeffrey E. Russel
*Attorney, Agent, or Firm*—Mary E. Gormley

[57] ABSTRACT

The invention relates to a compound having formula (I), wherein A, B, X, N, Z and Q are defined as described in the description. The compounds of the invention have anticoagulant activity and can be used in treating or preventing thrombin-related diseases.

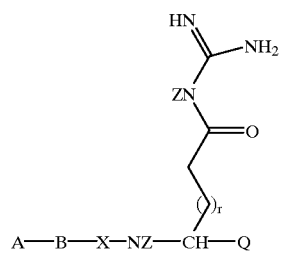

(I)

13 Claims, No Drawings

SERINE PROTEASE INHIBITORS

FIELD OF THE INVENTION

The invention relates to a serine protease inhibitor having an acylguanidine side chain, a pharmaceutical composition containing the same, as well as the use of said inhibitor for treating and preventing thrombin-related diseases.

BACKGROUND OF THE INVENTION

Serine proteases are enzymes which, amongst other things, play an important role in the blood coagulation cascade. Members of this group of proteases are for example thrombin, trypsin, factors VIIa, IXa, Xa, XIa, XIIa, and protein C.

Thrombin is the serine protease which regulates the last step in the coagulation cascade. The prime function of thrombin is the cleavage of fibrinogen to generate fibrin monomers, which form an insoluble gel by cross-linking. In addition, thrombin regulates its own production by activating factors V and VIII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation. Since inhibitors of thrombin may have a wide range of therapeutical applications, extensive research has been performed in this area.

In the development of synthetic inhibitors of serine proteases, and more specifically of thrombin, the interest in small synthetic peptides that are recognized by proteolytic enzymes in a manner similar to that of natural substrates, has increased. As a result, new peptide-like inhibitors have been prepared, such as the transition state inhibitors of thrombin and the low molecular weight thrombin inhibitor Inogatran (Thromb. Haemostas. 1995, 73:1325 (Abs. 1633); WO 93/11152 (Example 67)), which has been disclosed to be a potent and selective thrombin inhibitor. Related compounds are described in WO 95/23609; in comparison with Inogatran and its analogs, compounds disclosed in this patent application have an aromatic group in the agmatine-like group.

The search for more effective and more selective serine protease inhibitors continues unabated in order to obtain inhibitors which can be administered in lower dosages and which have fewer and less severe side effects.

SUMMARY OF THE INVENTION

A new class of highly potent serine protease inhibitors, in particular being selective thrombin or Xa inhibitors, has now been found, having the formula I

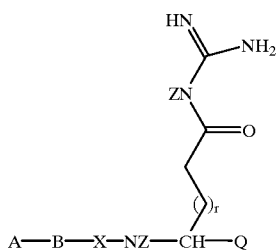

wherein

A is H, optionally substituted D,L α-hydroxyacetyl, $R^1$, $R^1$—O—C(O)—, $R^1$—C(O)—, $R^1$—SO$_2$—, $R^2$OOC—(CHR$^2$)$_{m-SO2}$—, $R^2$OOC—(CHR$^2$)$_m$—, $H_2$NCO—(CHR$^2$)$_m$—, or an N-protecting group, wherein $R^1$ is selected from (1–12C)alkyl, (2–12C)alkenyl, (2–12C)alkynyl and (3–8C)cycloalkyl, which groups may optionally be substituted with (3–8C)cycloalkyl, (1–6C)alkoxy, oxo, OH, COOH, CF$_3$ or halogen, and from (6–14C)aryl, (7–15C)aralkyl and (8–16C)aralkenyl, the aryl groups of which may optionally be substituted with (1–6C)alkyl, (3–8C)cycloalkyl, (1–6C)alkoxy, OH, COOH, CF$_3$ or halogen; each group $R^2$ is independently H or has the same meaning as $R^1$; m is 1, 2 or 3;

B is a bond, an amino-acid of the formula —NH—CH[(CH$_2$)$_p$C(O)OH]—C(O)— or an ester derivative thereof and p being 0, 1, 2 or 3, —N((1–12C)alkyl)—CH$_2$—CO—, —N((2–12C)alkenyl)—CH$_2$—CO—, —N((2–12C)alkynyl)—CH$_2$—CO—, —N(benzyl)—CH$_2$—CO—, D-1-Tiq, D-3-Tiq, D-Atc, Aic, D-1-Piq, D-3-Piq or a L- or D-amino acid having a hydrophobic, basic or neutral side chain, which amino acid may optionally be N—(1–6C)alkyl substituted; or A and B together are the residue $R^3R^4$N—CHR$^5$—C(O)—, wherein $R^3$ and $R^4$ independently are $R^1$, $R^1$—O—C(O)—, $R^1$—C(O)—, $R^1$—SO$_2$—, $R^2$OOC—(CHR$^2$)$_m$—SO$_2$—, $R^2$OOC—(CHR$^2$)$_m$—, $H_2$NCO—(CHR$^2$)$_m$—, or an N-protecting group, or one of $R^3$ and $R^4$ is connected with $R^5$ to form a 5- or 6-membered ring together with "N—C" to which they are bound, which ring may be fused with an aliphatic or aromatic 6-membered ring; and $R^5$ is a hydrophobic, basic or neutral side chain;

X is an L-amino acid with a hydrophobic side chain, serine, threonine, a cyclic amino acid optionally containing an additional heteroatom selected from N, O or S, and optionally substituted with (1–6C)alkyl, (1–6C)alkoxy, benzyloxy or oxo, or X is —NR$^2$—CH$_2$—C(O)— or the fragment

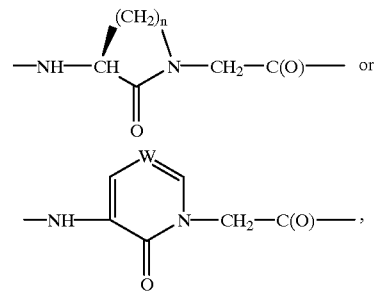

wherein n is 2, 3, or 4, and W is CH or N;

Q is H or —C(O)Y, wherein Y is H, —CHF$_2$, —CF$_3$, —CO—NH—(1–6C)alkylene—C$_6$H$_5$, —COOR$^6$ and $R^6$ being H or (1–6C)alkyl, —CONR$^7R^8$ and $R^7$ and $R^8$ being independently H or (1–6C)alkyl or $R^7$ and $R^8$ together being (3–6C)alkylene, or Y is a heterocycle selected from 2-thiazole, 2-thiazoline, 2-benzothiazole, 2-oxazole, 2-oxazoline and 2-benzoxazole, which heterocycles may optionally be substituted with (1–6C) alkyl, (1–6C)alkoxy or oxo;

Z is H or (1–6C)alkyl;

r is 0 or 1 if Q is —C(O)Y or r is 0, 1, 2, 3 or 4 if Q is H;

or a prodrug thereof or a pharmaceutically acceptable salt thereof.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery.

The compounds of the invention may also be used as in vitro anticoagulants.

DETAILED DESCRIPTION OF THE INVENTION

Preferred compounds according to the invention have the formula I, wherein X is an L-amino acid with a hydrophobic side chain, serine, threonine or —$NR^2$—$CH_2$—C(O)—; and Z is H or methyl Other preferred compounds of formula I are those, wherein A is as previously defined; B is a bond, an amino-acid of the formula —NH—CH[($CH_2$)$_p$C(O)OH]—C(O)— or an ester derivative thereof and p being 0, 1, 2 or 3, —N((1–6C)alkyl)—$CH_2$—CO—, —N((2–6C)alkenyl)—$CH_2$—CO—, —N(benzyl)—$CH_2$—CO—, D-1-Tiq, D-3-Tiq, D-Atc, Aic, D-1-Piq, D-3-Piq or a D-amino acid having a hydrophobic side chain, which amino acid may optionally be N-(1–6C)alkyl substituted; or A and B together are the residue $R^3R^4N$—$CHR^5$—C(O)—; and X is a cyclic amino acid optionally containing an additional heteroatom selected from N, O or S, and optionally substituted with (1–6C)alkyl, (1–6C)alkoxy, benzyloxy or oxo, or X is —$NR^2$—$CH_2$—C(O)— or the fragment

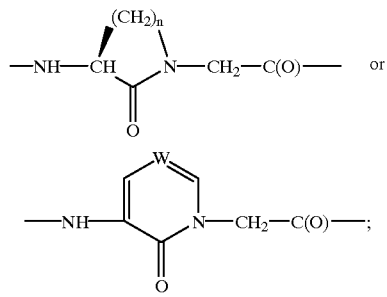

and Z is H or methyl.

More preferred are compounds of formula I, wherein A is H, 2-hydroxy-3-cyclohexyl-propionyl-, 9-hydroxy-fluorene-9-carboxyl, $R^1$, $R^1$—$SO_2$—, $R^2$OOC—$(CHR^2)_m$—$SO_2$—, $R^2$OOC—$(CHR^2)_m$—, $H_2$NCO—$(CHR^2)_m$—, or an N-protecting group, wherein $R^1$ is selected from (1–12C)alkyl, (2–12C)alkenyl, (6–14C)aryl, (7–15C)aralkyl and (8–16)aralkenyl; each group $R^2$ is independently H or has the same meaning as $R^1$, B is a bond, D-1-Tiq, D-3-Tiq, D-Atc, Aic, D-1-Piq, D-3-Piq or a D-amino acid having a hydrophobic side chain, which amino acid may optionally be N-(1–6C)alkyl substituted; or A and B together are the residue $R^3R^4N$—$CHR^5$—C(O)—; Y is —CO—NH—(1–6C)alkylene-$C_6H_5$, —$COOR^6$, —$CONR^7R^8$, or Y is a heterocycle select from 2-thiazole, 2-thiazoline, 2-benzothiazole, 2-oxazole, 2-oxazoline and 2-benzoxazole. In particular preferred are those compounds, wherein A is $R^1$—$SO_2$—, $R^2$OOC—$(CHR^2)_m$—, B is a bond, D-1-Tiq, D-3-Tiq, D-Atc, Aic, D-1-Piq, D-3-Piq or a D-amino acid having a hydrophobic side chain; or A and B together are the residue $R^3R^4N$—$CHR^5$—C(O)—, wherein at least one of $R^3$ and $R^4$ is $R^2$OOC—$(CHR^2)_m$— or $R^1$—$SO_2$— and the other independently is (1–12C)alkyl, (2–12C)alkenyl, (2–12C)alkynyl, (3–8C)cycloalkyl, (7–15C)aralkyl, $R^1$—$SO_2$— or $R^2$OOC—$(CHR^2)_m$—, and $R^5$ is a hydrophobic side chain; Y is —CO—NH—(1–6C)alkylene-$C_6H_5$, —$COOR^6$ and $R^6$ being H or (1–3C)alkyl, —$CONR^7R^8$, $R^7$ and $R^8$ being independently H or (1–3C)alkyl or $R^7$ and $R^8$ together being (3–5C)alkylene, or Y is a heterocycle selected from 2-thiazole, 2-benzothiazole, 2-oxazole or 2-benzoxazole.

When A is $R^2$OOC—$(CHR^2)_m$—, preferably B is a D-amino acid having a hydrophobic side chain; or A and B together are the residue $R^3R^4N$—$CHR^5$—C(O)—, wherein at least one of $R^3$ and $R^4$ is $R^2$OOC—$(CHR^2)_m$— and the other independently is (1–12C)alkyl, (3–8C)cycloalkyl, $R^1$—$SO_2$— or $R^2$OOC—$(CHR^2)_m$—, and X is 2-azetidine carboxylic acid, proline, pipecolic acid, 4-thiazolidine carboxylic acid, 3,4-dehydro-proline, 2-octahydroindole carboxylic acid. More preferred are compounds wherein A is HOOC—$CH_2$—; B is D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, D-Chg; or A and B together are the residue $R^3R^4N$—$CHR^5$—C(O)—, wherein at least one of $R^3$ and $R^4$ is HOOC—$CH_2$— and the other independently is methyl, (1–4C)alkyl—$SO_2$— or HOOC—$CH_2$— and $R^5$ is (3–8C)cycloalkyl, (3–8C)cycloalkyl(1–4C)alkyl, phenyl, benzyl, optionally substituted with chlorine or (1–4C) alkoxy.

When A is $R^1$—$SO_2$—, preferably B is a bond, D-1-Tiq, D-3-Tiq, D-Atc, Aic, D-1-Piq, D-3-Piq or a D-amino acid having a hydrophobic side chain; or A and B together are the residue $R^3R^4N$—$CHR^5$—C(O)—, wherein at least one of $R^3$ and $R^4$ is $R^1$—$SO_2$— and the other independently is (1–12C)alkyl or $R^1$—$SO_2$—; X is 2-azetidine carboxylic acid, proline, pipecolic acid, 4-thiazolidine carboxylic acid, 3,4-dehydro-proline, 2-octahydroindole carboxylic acid, or the fragment

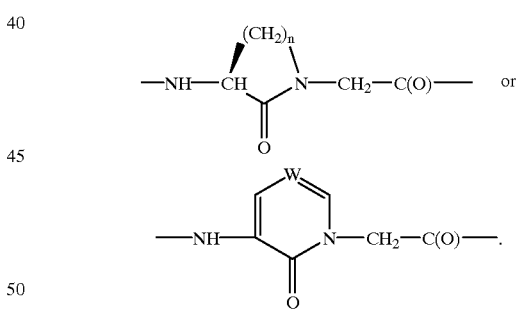

More preferred are compounds wherein A is Ethyl—$SO_2$— or Benzyl—$SO_2$—; B is a bond, D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, D-Chg; or A and B together are the residue $R^3R^4N$—$CHR^5$—C(O)—, wherein at least one of $R^3$ and $R^4$ is Ethyl—$SO_2$— or Benzyl—$SO_2$— and the other independently is (1–12C) alkyl or $R^1$—$SO_2$— and $R^5$ is (3–8C)cycloalkyl, (3–8C) cycloalkyl(1–4C)alkyl, phenyl, benzyl, diphenylmethinyl, which groups are optionally substituted with chlorine or (1–4C)alkoxy.

The most preferred compounds of formula I are those wherein Q is H and r is 0, 1 or 2.

The N-protecting group as defined in the definition of moiety A is any N-protecting group as used in peptides.

Suitable N-protecting groups can be found in T. W. Green and P. G. M. Wuts: Protective Groups in Organic Synthesis, Second Edition (Wiley, N.Y. 1991) and in The Peptides, Analysis, Synthesis, Biology, Vol. 3 E. Gross and J. Meienhofer, Eds., (Academic Press, New York, 1981).

The term optionally substituted D,L α-hydroxyacetyl means a group of the formula HO—CR$^a$R$^b$—C(O)—, wherein R$^a$ and R$^b$ independently are H, a hydrophobic side chain, or R$^a$ and R$^b$ together form a 5- or 6-membered ring, which is optionally fused with one or two aliphatic or aromatic 6-membered rings, and which 5- or 6-membered ring consists of carbon atoms and optionally one heteroatom selected from N, O and S. Preferred D,L α-hydroxyacetyl groups are 2-hydroxy-3-cyclohexyl-propionyl- and 9-hydroxy-fluorene-9-carboxyl.

The term (1–12C)alkyl means a branched or unbranched alkyl group having 1 to 12 carbon atoms, such as methyl, ethyl, t-butyl, isopentyl, heptyl, dodecyl, and the like. Preferred alkyl groups are (1–6C)alkyl groups, having 1–6 carbon atoms. Most preferred in the definition of R$^6$, R$^7$ and R$^8$ are (1–3C)alkyl groups, having 1–3 carbon atoms, such as methyl, ethyl, isopropyl. A (2–12C)alkenyl group is a branched or unbranched unsaturated hydrocarbon group having 2 to 12 carbon atoms. Preferred are (2–6C)alkenyl groups. Examples are ethenyl, propenyl, allyl, and the like.

The term (1–6C)alkylene means a branched or unbranched alkylene group having 1 to 6 carbon atoms, such as —(CH$_2$)$_m$— and m is 1 to 6, —CH(CH$_3$)—, —CH(CH$_3$)—(CH$_2$)—, etc. Preferred alkylene groups in the definition of Y are ethylene and methylene.

A (2–12C)alkynyl group is a branched or unbranched hydrocarbon group containing a triple bond and having 2 to 12 carbon atoms. Preferred are (2–6C)alkynyl groups, such as ethynyl and propynyl.

A (6–14C)aryl group is an aromatic moiety of 6 to 14 carbon atoms. The aryl group may further contain one or more hetero atoms, such as N, S, or O. Examples of aryl groups are phenyl, naphthyl, (iso)quinolyl, indanyl, and the like. Most preferred is the phenyl group. (7–15C)Aralkyl and (8–16C)aralkenyl groups are alkyl and alkenyl groups respectively, substituted by one or more aryl groups, the total number of carbon atoms being 7 to 15 and 8 to 16, respectively.

The term (1–6C)alkoxy means an alkoxy group having 1–6 carbon atoms, the alkyl moiety of which having the meaning as previously defined.

The term (3–8C)cycloalkyl means a cycloalkyl group having 3–8 carbon atoms, being cyclopropyl, cyclobutyl, cyclopentyl, cyclohexyl, cycloheptyl or cyclo-octyl. Cyclopentyl and cyclohexyl are preferred cycloalkyl groups.

The term halogen means fluorine, chlorine, bromine or iodine.

The term ester derivative means any appropriate ester derivative, preferably (1–4C)alkyl-esters, such as methyl-, ethyl- or t-butyl-esters.

The terms 1- and 3-Tiq mean 1,2,3,4-tetrahydroisoquinoline-1- or -3-carboxylic acid, respectively; 1- and 3-Piq are 1- and 3-carboxyperhydroisoquinoline, respectively; Atc is 2-aminotetralin-2-carboxylic acid; Aic is amino tetra-carboxylic acid; Phe is phenylalanine; Cha is cyclohexylalanine; Dpa is diphenylalanine; Coa is cyclooctylalanine; Chg is cyclohexylglycine; Nle is norleucine.

The term hydrophobic side chain means a (1–12C)alkyl, optionally substituted with one or more (3–8C)cycloalkyl groups or (6–14C)aryl groups (which may contain a heteroatom, e.g. nitrogen) such as cyclohexyl, cyclo-octyl, phenyl, pyridinyl, naphthyl, tetrahydronaphthyl, and the like, which hydrophobic side chain may optionally be substituted with substituents such as halogen, trifluoromethyl, lower alkyl (for instance methyl or ethyl), lower alkoxy (for instance methoxy), phenyloxy, benzyloxy, and the like.

The term substituted means: substituted by one or more substituent.

Amino acids having a basic side chain are for example, but not limited to, arginine and lysine, preferably arginine. The term amino acids having a neutral side chain refers to amino acids such as methionine sulphon and the like.

Cyclic amino acids are for example 2-azetidine carboxylic acid, proline, pipecolic acid, 1-amino-1-carboxy-(3–8C)cycloalkane (preferably 4C, 5C or 6C), 4-piperidine carboxylic acid, 4-thiazolidine carboxylic acid, 3,4-dehydroproline, azaproline, 2-octahydroindole carboxylic acid, and the like. Preferred are 2-azetidine carboxylic acid, proline, pipecolic acid, 4-thiazolidine carboxylic acid, 3,4-dehydroproline and 2-octahydroindole carboxylic acid. The term prodrug means a compound in which the amidine group of the compound of formula I is protected, e.g. by a hydroxy or (1–6C)alkoxycarbonyl group.

The invention further includes a process for preparing a compound of formula I, including coupling of suitably protected amino acids or amino acid analogs, followed by removing the protective groups.

The compounds according to formula I may be prepared in a manner conventional for such compounds.

To that end, suitably Nα protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert-butyloxycarbonyl group (Boc), benzyloxycarbonyl (Z) group and substituted analogs or the base-labile 9-fluorenyl-methyloxycarbonyl (Fmoc) group. The Z group can also be removed by catalytic hydrogenation. Other suitable amino protective groups include Nps, Bmv, Bpoc, Msc, etc. A good overview of amino protective groups is given is given in The Peptides, Analysis, Synthesis, Biology, Vol. 3 E. Gross and J. Meienhofer, Eds., (Academic Press, New York, 1981). Protection of carboxyl groups can take place by ester formation e.g. base-labile esters like methyl- or ethylesters, acid labile esters like tert-butylesters, or hydrogenolytically-labile esters like benzylesters. Protection of the side chain function of lysine may be accomplished by using the aforementioned groups. Activation of the carboxyl group of the suitably protected amino acids or peptides can take place by the azide, mixed anhydride, active ester, or carbodiimide method, especially with the addition of catalytic and racemization-suppressing compounds like 1-hydroxybenzotriazole, N-hydroxysuccinimide, 3-hydroxy4-oxo-3,4dihydro-1,2,3-benzotriazine, N-hydroxy-5-norbornene-2,3-dicarboximide. See, e.g. The Peptides, Analysis, Synthesis, Biology (see above) and Pure and Applied Chem. 59(3), 331–344 (1987). The acylguanidine moiety may be coupled to the C-terminus of suitably Nα-protected amino acid derivatives or peptides by coupling methods as described above.

In a suitable method to prepare the compounds of this invention wherein Q is —C(O)Y, protected glutamic acid (Glu) is coupled to the group Y, deprotected, followed by coupling at the N-terminus to the A-B-X- part of the molecule to form the compound of the formula A-B-X-Glu-Y. In a separate procedure, S-methylisourea is protected and converted into protected guanidine. The protected guanidine is coupled to A-B-X-Glu-Y, and after deprotection the compound of formula I is obtained.

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention may possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLES

The term "-Glu(guanidine)" means

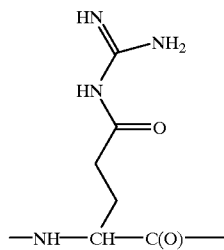

Bzl=benzyl; Boc=tert-butyloxycarbonyl; Cbz=benzyloxycarbonyl; Ac=acetyl; PAc=phenylacetyl; Glu=glutamic acid; Cha=cyclohexylalanine; Pro=proline; Phe=phenylalanine; 1-Piq=1-carboxyperhydroisoquinoline; Nal=2-naphthylalanine; Asp=aspartic acid If not indicated differently, the retention times (Rt (LC)) were determined by reversed phase liquid chromatography on a Supelcosil LC-18-DB (2.1 mm×25 cm) column.

Example 1

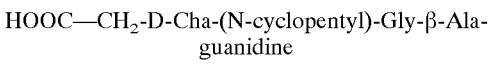

(a). N-(tert-butyloxycarbonyl)-S-methylisothiourea

S-Methylisothiourea semisulfate (10 g) was suspended in dichloromethane (100 ml). To the suspension, a 4N sodium hydroxide solution (10 ml) was added under stirring. The reaction mixture was placed in an ice bath; di-tert-butyl dicarbonate (15.7 g) in dichloromethane (100 ml) was added dropwise along with a 2N sodium hydroxide solution to keep the pH around 11. After the addition was completed, the reaction mixture was stirred overnight at room temperature. The dichloromethane layer was separated, and the aqueous layer was extracted with dichloromethane. The combined organic layers were washed with water and dried over sodium sulfate, filtered and evaporated in vacuo. The residue was purified by chromatography on silica (eluent: heptane/ethyl acetate=4/1 v/v %) to yield N-(tert-butyloxycarbonyl)-S-methylisothiourea (9.38 g).

TLC: $R_f$=0.75, silica gel, ethyl acetate/heptane=3/1 v/v %

(b). N-(benzyloxycarbonyl)-N'-(tert-butyloxycarbonyl)-S-methylisothiourea

N-(tert-butyloxycarbonyl)-S-methylisothiourea (2 g) was dissolved in dichloromethane (20 ml). To the solution, a 4N sodium hydroxide solution (2 ml) was added with stirring. The reaction mixture was placed in an ice bath; N-(benzyloxy-carbonyloxy)-succinimid (2.62 g) in dichloromethane (20 ml) was added dropwise together with a 2N sodium hydroxide solution to keep the pH around 11. After addition was complete, the reaction mixture was stirred overnight at room temperature. The dichloromethane layer was separated, and the aqueous layer was washed twice with dichloromethane. The combined organic layers were washed with water and dried over sodium sulfate, filtered and evaporated in vacuo. The residue was purified by chromatography on silica (eluent: heptane/ethyl acetate=3/2 v/v %) to yield N-(benzyloxy-carbonyl)-N'-(tert-butyloxycarbonyl)-S-methylisothiourea (3.15 g).

TLC: $R_f$=0.78, silica gel, ethyl acetate/heptane=1/1 v/v %

(c). N-(Cbz)-N'-(t-Boc)-guanidine

N-(Benzyloxycarbonyl)-N'-(tert-butyloxycarbonyl)-S-methylisothiourea (3.15 g) was dissolved in methanolic ammonia (2.4M, 50 ml). The reaction mixture was stirred overnight at room temperature. The mixture was evaporated in vacuo and the resulting residue was purified by chromatography on silica (eluent: dichloromethane/methanol=95/5 v/v %) to yield N-(Cbz)-N'-(t-Boc)-guanidine (1.83 g).

TLC: $R_f$=0.80, silica gel, dichloromethane/methanol=9/1 v/v %.

(d). N-(t-Boc)-guanidine hydrochloride

10% Palladium on charcoal (250 mg) and 3.12 ml of a 2N hydrochloride solution were added to a solution of N-(Cbz)-N'-(t-Boc)-guanidine (1.8 g) in methanol (50 ml). The mixture was hydrogenated at atmospheric pressure at room temperature for 1 h. The palladium catalyst was removed by filtration and the solvent was removed by evaporation at reduced pressure yielding N-(t-Boc)-guanidine.hydrochloride quantitatively.

TLC: $R_f$=0.10, silica gel, dichloromethane/methanol=9/1 v/v %.

(e). Cbz-β-Ala-(N-t-Boc)-guanidine

Cbz-β-Ala-OH (171 mg) was dissolved in dry dimethylformamide (5 ml). After addition of triethylamine (212 μl), the reaction mixture was placed under nitrogen and cooled to −15° C. Isobutylchloroformate (99 μl) was subsequently added and the mixture was allowed to stir for 15 min at −15° C. N-(t-Boc)-guanidine.hydrochloride (150 mg) and triethylamine (106 μl) were added to the cold mixture. The reaction mixture was stirred for 1 h at −15° C. and then kept at room temperature for 45 min. Triethylamine. hydrochloride was filtered off and the filtrate was evaporated to dryness. The residue was purified by chromatography on silica (eluent: dichloromethane/methanol=95/5 v/v %) to yield Cbz-β-Ala-(N-t-Boc)-guanidine (256 mg).

TLC: $R_f$=0.50, silica gel, dichloromethane/methanol=9/1 v/v %.

(f). H-β-Ala-(N-t-Boc)-guanidine hydrochloride

10% Palladium on charcoal (100 mg) and 300 μl of a 4M hydrochloride solution were added to a solution of Cbz-β-Ala-(N-t-Boc)-guanidine (220 mg) in dimethylformamide (5 ml). The mixture was hydrogenated at atmospheric pressure at room temperature for 1 h. The palladium catalyst was removed by filtration and the solvent was removed by evaporation at reduced pressure yielding H-β-Ala-(N-t-Boc)-guanidine hydrochloride quantitatively.

TLC: $R_f$=0.10, silica gel, dichloromethane/methanol=9/1 v/v %.

(g). N-Cyclopentyl-Gly-OMe

Cyclopentanone (15.6 g) was added to a solution of H-Gly-OMe.HCl (23.2 g) in 200 ml of methanol. The mixture was stirred for 15 minutes and sodium cyanoborohydride (7 g) was added. The pH was adjusted to 6. The reaction mixture was stirred for 16 hours at room temperature. To complete the reaction cyclopentanone (1 g) was added and stirring was continued.

The reaction was monitored on TLC. When all the starting material had disappeared, the mixture was acidified to pH 2 and was stirred for 30 minutes. The solvent was removed and the residue was diluted with water. The solution was washed with ether, the pH adjusted to 12 with 6N sodium hydroxide and extracted with dichloromethane. The combined organic layers were washed with a saturated sodium chloride solution, dried on sodium sulfate and evaporated in vacuo to yield 16 g of an oil.

Rf=0.46 in ethyl acetate/pyridine/acetic acid/water 63/20/6/11 (v/v/v/v) on silica.

(h). N-(t-Butyloxycarbonylmethyl-D-Cha-OMe t-Butyl-bromo acetate (17 g) was added to a stirred solution H-D-Cha-OMe.HCl (26 g) in 300 ml of acetonitrile. The pH of the mixture was adjusted to 8.5 with diisopropylethylamine. The mixture was stirred for 16 hours at room temperature and evaporated in vacuo. The residue was dissolved in dichloromethane and the solution was washed with water, dried on sodium sulfate and evaporated in vacuo. Chromatography over silica gel in hexane/ethyl acetate 9/1 (v/v) gave 20 g of N-(t-butyloxycarbonylmethyl)-D-Cha-OMe.

Rf=0.46 in ethyl acetate/pyridine/acetic acid/water 15¾/5/1½/2¾ (v/v/v/v) on silica.

(I). N-(t-Butyloxycarbonylmethyl)-N-Boc-D-Cha-OMe

The pH of a solution of N-(t-butyloxycarbonylmethyl)-D-Cha-OMe (20 g) and di-t-butyl dicarbonate (17 g) was adjusted to 8.5 with diisopropylethylamine. The mixture was stirred for 16 hours at room temperature. The solvent was removed in vacuo. Dichloromethane and water were added to the residue. The organic layer was separated, washed with cold 1N hydrogen chloride, water, 5% sodium hydrogen carbonate and water. The organic layer was dried on sodium sulfate and the filtrate was evaporated to an amorphous solid of N-(t-butyloxycarbonylmethyl)-N-Boc-D-Cha-OMe with a yield of 28 g.

Rf=0.60 in ethyl acetate/pyridine/acetic acid/water 252/20/6/11 (v/v/v/v) on silica.

(j). N-(t-Butyloxycarbonylmethyl)-N-Boc-D-Cha-OH

A solution of N-(t-butyloxycarbonylmethyl)-N-Boc-D-Cha-OMe (28 g) in 420 ml of dioxane:water 9/1 (v/v) was treated with sufficient 1N sodium hydroxide to keep the pH at 13 for 90 minutes at room temperature. After acidification, the mixture was poured into water and was extracted with dichloromethane. The organic layer was washed with water and was dried on sodium sulfate. The filtrate was evaporated and yielded 24 g of N-(t-butyloxycarbonylmethyl)-N-Boc-D-Cha-OH.

Rf=0.23 in dichloromethane/methanol 9/1 (v/v) on silica.

(k). N-(t-Butyloxycarbonylmethyl)-N-Boc-D-Cha-(N-cyclopentyl)-Gly-OMe

N-cyclopentyl-Gly-OMe (10.2 g) and 2-(1H-benzotriazol-1-yl)-1,1,3,3-tetramethyluronium tetrafluoroborate (TBTU; 21.2 g) were added to a solution of N-(t-butyloxycarbonylmethyl)-N-Boc-D-Cha-OH (24 g) in 300 ml of N,N-dimethyl formamide. The pH of the mixture was adjusted to 8.5. The mixture was stirred overnight at room temperature and was concentrated by evaporation. Water and ethyl acetate were added to the residue. The organic layer was separated and washed with 1N hydrogen chloride, water, 5% sodium hydrogen carbonate and water and dried over sodium sulfate. The filtrate was evaporated and the residue was chromatographed on silica gel in hexane/ethyl acetate 8/2 (v/v) as eluent. The fractions containing N-(t-butyloxycarbonylmethyl)-N-Boc-D-Cha-(N-cyclopentyl)-Gly-OMe were pooled and evaporated. Yield: 17 g.

Rf=0.57 in hexane/ethyl acetate 7/3 (v/v) on silica.

(l). N-(t-Butyloxycarbonylmethyl)-N-Boc-D-Cha-(N-cyclopentyl)-Gly-OH

N-(t-butyloxycarbonylmethyl)-N-Boc-D-Cha-(N-cyclopentyl)-Gly-OMe (17 g) was saponified in a mixture of dioxane/water 1/1 (v/v, 150 ml) and diluted sodium hydroxide and yielded 15 g of an amorphous solid. Chromatography over silica gel with dichloromethane/methanol 95/5 (v/v) as eluent gave 13 g of N-(t-butyloxycarbonylmethyl)-N-Boc-D-Cha-(N-cyclopentyl)-Gly-OH.

Rf=0.30 in dichloromethane/methanol 9/1 (v/v) on silica.

(m). N-(t-Butyloxycarbonylmethyl)-N-Boc-D-Cha-(N-cyclopentyl)-Gly-β-Ala-N-t-Boc)-guanidine N-(t-Butyloxycarbonylmethyl)-N-Boc-D-Cha-(N-cyclopentyl)-Gly-OH (310 mg) was dissolved in dry dimethylformamide (10 ml). After addition of triethylamine (168 μl), the reaction mixture was placed under nitrogen and cooled to −15° C. Isobutylchloroformate (79 μl) was subsequently added and the mixture was allowed to stir for 15 min at −15° C. H-β-Ala-(N-t-Boc)-guanidine. hydrochloride (154 mg) was dissolved in dry dimethylformamide (5 ml) and added dropwise to the cold mixed anhydride solution, maintaining the pH at 8.5 by addition of triethylamine. The reaction mixture was stirred for 1 h at −15° C. and then at 0° C. for 1 h. The reaction mixture was evaporated to dryness. The residue was dissolved in ethyl acetate and successively washed with water, brine, dried over sodium sulfate and concentrated in vacuo. The residue was purified by chromatography on silica (eluent: dichloromethane/methanol=95/5 v/v %) to yield N-(t-butyloxycarbonylmethyl)-N-Boc-D-Cha-(N-cyclopentyl)-Gly-β-Ala-(N-t-Boc)-guanidine (268 mg).

TLC: $R_f$=0.80, silica gel, dichloromethane/methanol=9/1 v/v %.

(n). HOOC-CH$_2$-D-Cha-N-cyclopentyl)-Gly-β-Ala-guanidine

N-(t-Butyloxycarbonylmethyl)-N-Boc-D-Cha-(N-cyclopentyl)-Gly-β-Ala-(N-t-Boc)-guanidine (265 mg) was treated with 90% trifluoroacetic acid/water (10 ml) for 2 h at room temperature. The reaction mixture was concentrated in vacuo and the residue dissolved in water and directly charged onto a preparative HLPC Supelcosil LC-18-DB column using a gradient elution system of 20% A/80% B to 20% A/20% B/60% C over 40 min at a flow rate of 15 ml/min (A: 0.5M phosphate buffer pH=2.1, B: water, C: acetonitril/water=6/4). Yield: 185 mg of HOOC-CH$_2$-D-Cha-(N-cyclopentyl)-Gly-β-Ala-guanidine.

$R_t$(LC): 32.22 min 20% A/80% B to 20% A/20% B/60% C in 40 min.

Example 2

HOOC-CH$_2$-D-Cha-Pro-Glu(guanadine)-(2-thiazolyl)

(a). H-D-Cha-OMe.HCl

To cold (−20° C.) and dry methanol (195 ml) was added dropwise thionylchloride (28 ml). H-D-Cha-OH.HCl (40 g) was added and the reaction mixture was heated under reflux for 5 h. The mixture was concentrated in vacuo and coevaporated with methanol (3 times). The residue was crystallized from methanol/diethylether yielding H-D-Cha-OMe.HCl as a crystalline powder (40.9 g).

TLC: $R_f$=0.66, silica gel, n-butanol/acetic acid/water=10/1/3 v/v/v %.

(b). N-(t-Butyloxycarbonylmethyl)-D-Cha-OMe t-Butyl-bromo acetate (36 g) was added to a stirred solution H-D-Cha-OMe.HCl (40.9 g) in 400 ml of acetonitrile. The pH of the mixture was adjusted to 8.5 with diisopropylethylamine. The mixture was stirred for 16 hours at room temperature and evaporated in vacuo. The residue was dissolved in dichloromethane and the solution was washed with water, dried on sodium sulfate and evaporated in vacuo. Chromatography over silica gel in heptane/ethyl acetate 9/1 (v/v) gave 64 g of N-(t-butyloxycarbonylmethyl)-D-Cha-OMe.

TLC:$R_f$=0.25, silica gel, ethyl acetate/heptane=1/1 v/v %.

(c). N-(t-Butyloxycarbonylmethyl)-N-Boc-D-Cha-OMe

The pH of a solution of N-(t-butyloxycarbonylmethyl)-D-Cha-OMe (64 g) and di-t-butyl dicarbonate (40.3 g) was adjusted to 8.5 with diisopropylethylamine. The mixture was stirred for 16 hours at room temperature. The solvent was removed in vacuo. Dichloromethane and water were added to the residue. The organic layer was separated, washed with cold IN hydrogen chloride, water, 5% sodium hydrogen carbonate and water. The organic layer was dried on sodium sulfate and the filtrate was evaporated to an amorphous solid of N-(t-butyloxycarbonylmethyl)-N-Boc-D-Cha-OMe with a yield of 59.6 g.

TLC: $R_f$=0.50, silica gel, ethyl acetate/heptane=1/1 v/v %.

(d). N-(t-Butyloxycarbonylmethyl)-N-Boc-D-Cha-OH

A solution of N-(t-Butyloxycarbonylmethyl)-N-Boc-D-Cha-OMe (59.6 g) in 906 ml of dioxane/water=9/1 (v/v) was treated with sufficient 6N sodium hydroxide to keep the pH at 12 for 6 hours at room temperature. After acidification, the mixture was poured into water and was extracted with dichloromethane. The organic layer was washed with water and was dried on sodium sulfate. The filtrate was evaporated and yielded 54 g of N-(t-butyloxycarbonylmethyl)-N-Boc-D-Cha-OH.

TLC: $R_f$=0.60, silica gel, dichloromethane/methanol=9/1 v/v %.

(e). N-(t-Butyloxycarbonylmethyl)-N-Boc-D-Cha-Pro-OBzl

To a cold (0° C.) solution of N-(t-Butyloxycarbonylmethyl)-N-Boc-D-Cha-OH (13.5 g) in N,N-dimethyl formamide (150 ml) were successively added 1-hydroxy benzotriazole (7.09 g), dicyclohexyl carbodiimide (7.61 g), H-Pro-OBzl.HCl (9.31 g) and triethylamine (6 ml). The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogen carbonate, water, 3% citric acid and brine, dried over sodium sulfate and concentrated in vacuo. The residue was chromatographed on silica gel in heptane/ethyl acetate=3/1 (v/v) as eluent. The fractions containing N-(t-butyloxycarbonylmethyl)-N-Boc-D-Cha-Pro-OBzl were pooled and evaporated. Yield: 15 g.

TLC: $R_f$=0.70, silica gel, heptane/ethyl acetate=1/1 v/v %.

(f). N-(t-Butyloxycarbonylmethyl)-N-Boc-D-Cha-Pro-OH

10% palladium on charcoal (750 mg) was added to a solution of N-(t-butyloxy-carbonylmethyl)-N-Boc-D-Cha-Pro-OBzl (15 g) in methanol (150 ml). The mixture was hydrogenated at atmospheric pressure at room temperature for 1 hour. The palladium catalyst was removed by filtration and the solvent was removed by evaporation at reduced pressure yielding 11.2 g of N-(t-butyloxycarbonylmethyl)-N-Boc-D-Cha-Pro-OH.

TLC: $R_f$=0.65, silica gel, ethyl acetate/pyridine/acetic acid/water=213/20/6/11 v/v %.

(g). Boc-Glu(OtBu)-NMeOMe

To a solution of Boc-Glu(OtBu)-OH (15 g) in dichloromethane (150 ml) was added N,O-dimethyl-hydroxylamine hydrochloride (5.3 g) and [2-(1H-benzotriazol-1-yl)-1,1,3,3-tetramethyluronium tetrafluoroborate] (15.87 g) and the pH was adjusted to pH 8–8.5 by adding triethylamine. The reaction mixture was stirred for 16 h at room temperature. The mixture was washed successively with cold 0.3M hydrochloric acid solution, water, 5% aqueous sodium hydrogen carbonate solution and water. The organic layer was dried over sodium sulfate, filtered and evaporated. The residue was purified by chromatography on silica (eluent: dichloromethane/methanol=98/2 v/v %) to yield Boc-Glu(OtBu)-NMeOMe (17.5 g).

TLC: $R_f$=0.85, silica gel, dichloromethane/methanol=9/1 v/v %.

(h). Boc-Glu(OtBu)-(2-thiazolyl)

To a cold (−78° C.), stirred solution of n-butyllithium (88.9 mmol) in diethyl ether (90.7 ml), was added, dropwise, a solution of 2-bromothiazole (14.6 g) in diethyl ether (75 ml). After the solution had been stirred at −78° C. for 30 min, the solution was added dropwise to a solution of Boc-Glu(OtBu)-NMeOMe (14 g) in dry tetrahydrofuran (150 ml). The mixture was stirred at −78° C. for 1 h, then the mixture was poored into an ice-cold 5% aqueous citric acid solution. The mixture was allowed to warm to room temperature and the layers were separated. The aqueous layer was extracted with ethyl acetate. The combined organic layers were washed with water, saturated aqueous sodium chloride solution, dried over sodium sulfate, filtered and evaporated. The residue was purified by chromatography on silica (eluent: dichloromethane/ethylacetate=9/1 v/v %) to yield Boc-Glu(OtBu)-(2-thiazolyl) (6.83 g).

TLC: $R_f$=0.92, silica gel, dichloromethane/ethylacetate= 7/3 v/v %.

(i). H-Glu-(2-thiazolyl).TFA

Boc-Glu(OtBu)-(2-thiazolyl) (450 mg) was dissolved in 3 ml trifluoroacetic acid (TFA), 1 ml dichloromethane and 150 μl anisole and stirred for 1 h at room temperature. The crude amine was isolated as a yellow oil in quantitative yield after removal of the solvent by evaporation, and used immediately to prepare N-Boc-N-(tert-butyloxycarbonylmethyl)-D-Cha-Pro-Glu-(2-thiazolyl).

TLC: $R_f$=0.10, silica gel, ethyl acetate/pyridine/acetic acid/water=63/20/6/11 v/v/v/v %.

(j). N-(t-Butyloxycarbonylmethyl)-N-Boc-D-Cha-Pro-Glu-(2-thiazolyl)

N-Boc-N-(tert-butyloxycarbonylmethyl)-D-Cha-Pro-OH (590 mg) was dissolved in dry dimethyl formamide (15 ml). After addition of diisopropylethyl amine (416 μl), the reaction mixture was placed under nitrogen and cooled to −15° C. Isobutyl chloroformate (158 μl) was subsequently added and the mixture was allowed to stir for 15 min at −15° C. H-Glu-(2-thiazolyl).TFA (300 mg) was dissolved in dry dimethyl formamide (10 ml) and added dropwise to the cold mixed anhydride solution, maintaining the pH at 8.5 by addition of diisopropylethyl amine. The reaction mixture was stirred for 30 min at −15° C. The reaction mixture was evaporated to dryness. The residue was dissolved in ethyl acetate and successively washed with water, 5% aqueous sodium hydrogen carbonate solution, water, brine, dried over sodium sulphate and concentrated in vacuo. The residue was purified by chromatography on silica (eluent: dichloromethane/methanol=95/5 v/v %) to yield N-Boc-N-(tert-butyloxycarbonyl-methyl)-D-Cha-Pro-Glu-(2-thiazolyl) (171 mg).

TLC: $R_f$=0.50, silica gel, dichloromethane/methanol=9/1 v/v %.

(k). N-(tert-butyloxycarbonyl)-S-methylisothiourea

S-Methylisothiourea semisulfate (10 g) was suspended in dichloromethane (100 ml). To the suspension, 4N NaOH-solution (10 ml) was added with stirring. The reaction mixture was placed on an ice bath, di-tert-butyl dicarbonate (15.7 g) in dichloromethane (100 ml) was added dropwise along with 2N sodium hydroxide solution to keep the pH around 11. After the addition was complete, the reaction mixture was stirred overnight at room temperature. The dichloromethane layer was separated, and the aqueous layer was extracted twice with dichloromethane. The combined organic layers were washed with water and dried over sodium sulfate, filtered and evaporated in vacuo. The residue was purified by chromatography on silica (eluent: heptane/ethyl acetate=4/1 v/v %) to yield 9.38 g.

TLC: $R_f$=0.75, silica gel, ethyl acetate/heptane=311 v/v %

(l). N-(benzyloxycarbonyl)-N'-(tert-butyloxycarbonyl)-S-methylisothiourea

N-(tert-butyloxycarbonyl)-S-methylisothiourea (2 g) was dissolved in dichloromethane (20 ml). To the solution a 4N sodium hydroxide solution (2 ml) was added with stirring. The reaction mixture was placed on an ice bath, N-(benzyloxy-carbonyloxy)-succinimid (2.62 g) in dichloromethane (20 ml) was added dropwise along with 2N sodium hydroxide solution to keep the pH around 11. After the addition was complete, the reaction mixture was stirred overnight at room temperature. The dichloromethane layer was separated, and the aqueous layer was washed twice with dichloromethane. The combined organic layers were washed with water and dried over sodium sulfate, filtered and evaporated in vacuo. The residue was purified by chromatography on silica (eluent: heptane/ethyl acetate=3/2 v/v %) to yield 3.15 g.

TLC: $R_f$=0.78, silica gel, ethylacetate/heptane=1/1 v/v % (m). N-(Cbz)-N'-(t-Boc)-guanidine N-(benzyloxycarbonyl)-N'-(tert-butyloxycarbonyl)-S-methylisothiourea (3.15 g) was dissolved in methanolic ammonia (2.4M, 50 ml). The reaction mixture was stirred at room temperature overnight. The mixture was evaporated in vacuo and the resulting residue was purified by chromatography on silica (eluent: dichloromethane/ methanol=95/5 v/v %) to yield 1.83 g.

TLC: $R_f$=0.80, silica gel, dichloromethane/methanol=9/1 v/v %.

(n). N-(t-Boc)-guanidine.hydrochloride

To a solution of N-(Cbz)-N'-(t-Boc)-guanidine (1.8 g) in methanol (50 ml) was added 10% palladium on charcoal (250 mg) and 3.12 ml 2N hydrogen chloride solution. The mixture was hydrogenated at atmospheric pressure and at room temperature for 1 h. The palladium catalyst was removed by filtration and the solvent removed by evaporation at reduced pressure yielding N-(t-Boc)-guanidine.hydrochloride quantitatively.

TLC: $R_f$=0.10, silica gel, dichloromethane/methanol=9/1 v/v %.

(o). N-(t-Butyloxycarbonylmethyl)-N-Boc-D-Cha-Pro-Glu (N-t-Boc)-guanidin)-(2-thiazolyl)

To a cold (0° C.) solution of N-(t-Butyloxycarbonylmethyl)-N-Boc-D-Cha-Pro-Glu-(2-thiazolyl) (170 mg) in dichloromethane (5 ml) were successively added dicyclohexyl carbodiimide (123 mg), N-(t-Boc)-guanidine.HCl (75 mg) and triethylamine (53 μl). The mixture was stirred at 0° C. for 1 hour and then kept at room temperature for another hour. The mixture was cooled to −20° C. and dicyclohexylurea was removed by filtration. The filtrate was evaporated to dryness. The residue was chromatographed on silica gel in dichloromethane/methanol=95/5 (v/v %) as eluent. The fractions containing N-(t-Butyloxycarbonylmethyl)-N-Boc-D-Cha-Pro-Glu((,N-t-Boc)-guanidine)-(2-thiazolyl) were pooled and evaporated. Yield: 173 mg.

TLC: $R_f$=0.50, silica gel, dichloromethane/methanol=9/1 v/v %.

(p). HOOC-CH$_2$-D-Cha-Pro-Glu(guanidine)-(2-thiazolyl)

N-(t-Butyloxycarbonylmethyl)-N-Boc-D-Cha-Pro-Glu ((N-t-Boc)-guanidine)-(2-thiazolyl) was treated with 90% trifluoroacetic acid/water (10 ml) for 2.5 h. at room temperature. The reaction mixture was concentrated in vacuo and the residue dissolved in water and directly charged onto a preparative HPLC DeltaPak RP-C$_{18}$ using a gradient elution system of 20% A/80% B to 20% A/45% B/35% C over 40 min at a flow rate of 50 ml/min (A:0.5M phosphate buffer pH 2.1, B: water, C: acetonitril/water=6/4). Yield:22 mg of HOOC-CH$_2$-D-Cha-Pro-Glu(guanidine)-(2-thiazolyl).

Rt(LC): 35.04 min, A 20%, B 80%, C 0% to A 20%, B 20%, C 60% in 40 min.

Example 3

(4aR,8aR)-perhydroisoguinoline-1(R,S)-carbonyl-Pro-Glu(guanidine)-(2-thinzolyl)

(a). 2-Cbz-(4aR,8aR)-perhydroisoquinoline-1(R,S)-carboxylic acid

2-Cbz-(4aR,8aR)-perhydroisoquinoline-1(R,S)-carboxylic acid has been synthesised as described in EP 0643073, example 1.

TLC: Rf=0.85, ethylacetate/pyridine/acetic acid/water 63/20/6/11 on silica.

(b). 2-Cbz-(4aR,8aR)-perhydroisoquinoline-1(R,S)-carbonyl-Pro-OtBu.

To a cold solution (0 °C.) of 2-Cbz-(4aR,8aR)-perhydroisoquinoline-1(R,S)-carboxylic acid (500 mg) in dimethylformamide (5 ml) were successively added DCCI (1,3-dicyclohexylcarbodiimide; 342 mg), HOBT (1-hydroxybenzotriazole hydrate; 319 mg), H-Pro-OtBu. (270 mg) and triethylamine (0.55 ml). The reaction mixture was stirred at 0 °C. for 1 h. and then kept at room temperature overnight. The reaction mixture was cooled to −20 °C. and the DCU (1,3-dicyclohexylurea) was removed by filtration. The filtrate was concentrated in vacuo and the residue was dissolved in ethylacetate. This solution was washed successively with 5% aqueous sodium hydrogencarbonate solution, 3% aqueous citric acid solution, water and brine, dried over sodium sulphate and concentrated in vacuo. The residue was purified by chromatography on silica (eluent: heptane/ethylacetate 4/1 v/v %) to yield 2-Cbz-(4aR,8aR)-perhydroisoquinoline-1 (R,S)-carbonyl-Pro-O-tBu)(634 mg).

TLC: Rf=0.90, ethylacetate/pyridine/acetic acid/water 63/20/6/11 on silica.

(c). 2-Cbz-(4aR, 8aR)-perhydroisoquinoline-1(R,S)-carbonyl-Pro-OH

2-Cbz-(4aR,8aR)-perhydroisoquinoline-1(R,S)-carbonyl-Pro-O-t-butyl ester (600 mg) was stirred in a mixture of dichloromethane (1 ml), trifluoroacetic acid (3 ml), anisole (0.15 ml) for 1 h. at room temperature. The reaction mixture was concentrated in vacuo at low temperature and the residue was dissolved in water at pH of 9.5. The aqueous phase was washed with diethylether, whereafter the aqueous layer was acidified to pH 2.5 by 2M hydrochloric acid solution. The aqueous layer was extracted with ethylacetate and the organic phase was washed with brine, dried over sodium sulphate and concentrated in vacuo to yield 2-Cbz-(4aR,8aR)-perhydroisoquinoline-1(R,S)-carbonyl-Pro-OH (588 mg).

TLC: Rf=0.54, ethylacetate/pyridine/acetic acid/water 60/3/1/2 on silica (d). (4aR, 8aR)-perhydroisoquinoline-1(R,S)-carbonyl-Pro-Glu-(2-thiazolyl)

The mixed anhydride coupling between 2-Cbz-(4aR, 8aR)-perhydroisoquinoline-1(R,S)-carbonyl-Pro-OH and H-Glu-(2-thiazolyl).TFA, the guanidation, the deprotection and the purification were done according to the procedures described in example 2. Yield: 64.7 mg. Rt(LC): 28.93 min, 20% A,80% B to 20% A, 20% B and 60% C in 40 min.

Example 4

EtSO$_2$-D-Cha-Pro-Glu(guanidine)-(2-thiazolyl)

(a). Boc-D-Cha-Pro-OPAc

Boc-D-Cha-Pro-OPAc was prepared according a similar manner as described in example 1 using Boc-D-Cha-OH and H-Pro-OPAc.

TLC: Rf=0.5, dichloromethane/methanol 95/5 on silica (b). EthylSO$_2$-D-Cha-Pro-OPAc Boc-D-Cha-Pro-OPAc (3.8 g) was dissolved in 50% TFA/dichloromethane (25 ml) and stirred for 30 minutes at room temperature. The reaction mixture was evaporated in vacuo. The crude amine was dissolved in dichloromethane (50 ml) and ethanesulphonylchloride (0.8 ml) was added at −78° C. Triethylamine was added to keep the pH at 8 during the reaction. The mixture was stirred for 3 h. at 0° C., whereafter water (25 ml) was added. After an additional stirring for 30 minutes at room temperature, the reaction mixture was concentrated in vacuo. The residue was dissolved in diethylether and washed with IN hydrochloric acid solution, water, 5% sodium hydrogencarbonate solution and brine, dried over sodium sulphate, filtered and evaporated in vacuo. Trituration of the crude material with methanol yielded EthylSO$_2$-D-Cha-Pro-OPAc (3.0 g). TLC: Rf=0.6, dichloromethane/methanol 95/5 on silica.

(c). EthylSO$_2$-D-Cha-Pro-OH

To a solution of EthylSO$_2$-D-Cha-Pro-OPAc (10 g) in tetrahydrofuran (250 ml) was added 1M solution of tetrabutylammonium fluoride in tetrahydrofuran (84 ml). The reaction mixture was stirred for 30 minutes at room temperature and poured into water (1l). The aqueous solution was extracted with ethylacetate. The combined organic layers were successively washed with 1N hydrochloric acid solution and water, dried over sodium sulphate and concentrated in vacuo. The residue was purified by crystallisation from ethylacetate/diisopropylether to yield EthylSO$_2$-D-Cha-Pro-OH (6.0 g).

TLC: Rf=0.2, ethylacetate/pyridine/acetic acid/water 163/20/6/11 on silica.

(d). EthylSO$_2$-D-Cha-Pro-Glu(guanidine)-(2-thiazolyl)

The mixed anhydride coupling between EthylSO$_2$-D-Cha-Pro-OH and H-Glu-(2-thiazolyl). TFA, the guanidation, the deprotection and the purification were done according to the procedures described in example 2. Yield: 83 mg.

Rt (LC): 28.33 min, 20% A,60% B and 20% C to 20% A and 80% C in 30 min.

Example 5

N-Ac-D-Phe-2-Nal-Glu(guanidine)-(2-thiazolyl)

N-Ac-D-Phe-2-Nal-OMe was prepared according a similar manner as described in example 2 using N-Ac-D-Phe-OH and H-2-Nal-OMe.

(a). N-Ac-D-Phe-2-Nal-OH

A solution of N-Ac-D-Phe-2-Nal-OMe (1.55 g) in 20 ml of dioxane/water=9/1 (v/v) was treated with sufficient 6N sodium hydroxide to keep the pH at 12 for 1 hours at room temperature. After acidification, the mixture was poured into water and was extracted with dichloromethane. The organic layer was washed with water and was dried on sodium sulfate. The filtrate was evaporated and yielded 1.7 g crude N-Ac-D-Phe-2-Nal-OH.

TLC: R$_f$=0.50, silica gel, ethyl acetate/pyridinelacetic acid/water=63/20/6/1 1 v/v/v/v %.

(b). N-Ac-D-Phe-2-Nal-Glu(guanidine)-(2-thiazolyl)

The mixed anhydride coupling between N-Ac-D-Phe-2-Nal-OH and H-Glu-(2-thiazolyl).TFA, the guanidation, the deprotection and the purification were done according to the procedures described in example 2. Yield: 218 mg.

Rt(LC): 29.97 min, 20% A, 60% B and 20% C to 20% A and 80% C in 30 min.

Example 6

N-Me-D-Cha-Pro-Glu(guanidine)-(2-thiazolyl)

Boc-(N-Me)-D-Cha-Pro-OH was prepared according a similar manner as described in example 2 using Boc-(N-Me)-D-Cha-OH and H-Pro-OBzl.

H-(N-Me)-D-Cha-Pro-Glu(guanidine)-(2-thiazolyl)

The mixed anhydride coupling between Boc-(N-Me)-D-Cha-Pro-OH and H-Glu-(2-thiazolyl). TFA, the guanidation, the deprotection and the purification were done according to the procedures described in example 2. Yield: 85 mg.

Rt(LC): 32.27 min, 20% A and 80% B to 20% A, 20%B and 60% C in 40 min.

Example 7

N-Ac-D-Phe-Phe-Glu(guanidine)-(2-thiazolyl)

The title compound was prepared in an analogous procedure as described in example 5. Yield: 112 mg. Rt (LC): 42.97 min, 20% A, 80% B to 20% A, 20% B and 60% C in 40 min.

Example 8

N-MeD-Phe-Pro-Glu(guanidine)-(2-thiazolyl)

Boc-(N-Me)-D-Phe-Pro-OMe was prepared according a similar manner as described in example 2 using Boc-(N-Me)-D-Cha-OH and H-Pro-OMe.

Boc-(N-Me)-D-Phe-Pro-OH was prepared according to a similar manner as described in example 5 using Boc-(N-Me)-D-Phe-Pro-OMe.

Rt(LC): 28.0 min, 20% A, 80% B to 20% A, 20%B and 60% C in 40 min.

H-(N-Me)-D-Phe-Pro-Glu(guanidine)-(2-thiazolyl)

The mixed anhydride coupling between Boc-(N-Me)-D-Phe-Pro-OH and H-Glu-(2-thiazolyl). TFA, the guanidation, the deprotection and the purification were done according to the procedures described in example 2. Yield: 79.3 mg.

Rt(LC): 28.28 min, 20% A, 80% B to 20% A, 20%B and 60% C in 40 min.

Example 9

BzlSO$_2$-norLeu(cyclo)-Gly-Glu(guanidine)-(2-thiazolyl)

norLeu(cyclo)-Gly means a structural fragment of the formula

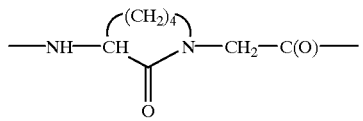

(a). Boc-norLeu(cyclo)-OH.

To a stirred solution of L-α-Amino-ε-caprolactam (10 g) in dioxane/water (2/1 v/v) (30 ml) was added 1N sodium hydroxide solution (7.8 ml) followed by di-t-butyl carbonate (18.8 g). The mixture was stirred for 16 h. at room temperature and concentrated in vacuo. The residue was dissolved in ethylacetate and washed with water and brine, dried over sodium sulphate, filtered and evaporated in vacuo. The crude material was triturated by hexane, filtered and dried in vacuo to yield Boc-norLeu(cyclo)-OH (16 g).

TLC: Rf=0.85, ethylacetate/heptane 1/1 on silica.

(b). Boc-norLeu(cyclo)-Gly-OMe.

Boc-norLeu(cyclo)-OH (10 g) was dissolved in dichloromethane (100 ml). At −20° C. a 1M solution of bis (trimethylsilyl)amide in THF/cyclohexane (1/1 v/v) (1 equiv.) was added slowly and the mixture was stirred for 30 min. Methyl bromoacetate (4 ml) was subsequently added and the mixture was stirred for 2 h. at room temperature. Additional bis (trimethylsilyl)amide in THF/cyclohexane (1/1 v/v) was added to force the reaction to completion. The mixture was diluted by dichloromethane and washed with 0.1N hydrochloric acid solution, water, 5% aqueous sodium bicarbonate solution and brine, dried over sodium sulphate, filtered and evaporated in vacuo. The residue was purified by chromatography on silica (eluent: heptane/ethylacetate 6/4 v/v%. to yield Boc-norLeu(cyclo)-Gly-OMe (12 g)

TLC: Rf=0.55, ethylacetate/heptane 6/4 on silica.

(c). BzlSO$_2$-norLeu(cyclo)-Gly-OMe.

Boc-norLeu(cyclo)-Gly-OMe (3 g) was dissolved in 50% TFA/dichloromethane (30 ml) and stirred for 1 h. at room temperature. The reaction mixture was evaporated in vacuo. The crude amine was dissolved in dichloromethane (25 ml) and a solution of benzylsulphonylchloride (2.25 g) in dichloromethane (10 ml) was added slowly at 0° C. Triethylamine was added to keep the pH at 8 during the reaction. The mixture was stirred for 1 h. at room temperature, whereafter the mixture was concentrated in vacuo. The residue was dissolved in ethylacetate and washed with 5% sodium hydrogencarbonate solution, water and brine, dried over sodium sulphate, filtered and evaporated in vacuo. The residue was purified by chromatography on silica (eluent: dichloromethane/ethylacetate 95/5 v/v%. to yield Bz/SO$_2$-norLeu(cyclo)-Gly-OMe (3.9 g)

TLC: Rf=0.40, dichloromethane/ethylacetate 9/1 on silica.

(d). BzlSO$_2$-norLeu(cyclo)-Gly-OH.

A solution of BzlSO$_2$-norLeu(cyclo)-Gly-OMe (3.9 g) in 100 ml of dioxane/water 9/1 was treated with sufficient 1N sodium hydroxide to keep the pH at 13 for 2 hours at room temperature. After acidification, the mixture was poured into water and extracted with dichloromethane. The organic layer was washed with water and dried on sodium sulphate. The filtrate was evaporated and yielded 3.6 g of the title compound.

TLC: Rf=0.60, ethylacetate/pyridine/acetic acid/water 63/20/6/11 on silica.

(e). BzlSO$_2$-norLeu(cyclo)-Gly-Glu(guanidine)-(2-thiazolyl)

The mixed anhydride coupling between BzlSO$_2$-norLeu (cyclo)-Gly-OH and H-Glu-(2-thiazolyl). TFA, the guanidation, the deprotection and the purification were done according to the procedures described in example 2. Yield: 34.6 mg.

Rt (LC): 21.42 min, 20% A, 60% B and 20% C to 20% A and 80% C in 30 min.

Example 10

Preparation of Acylguanidines on Kaiser Oxime Resin

To a suspension of 4.0 grams of Kaiser oxime resin (NovaBiochem, 1.10 mmol/gram) in 80 ml of dichloromethane/dimethyl formamide (3:2 v/v) were added Boc-β-Ala-OH (3.3 g, 17.6 mmol), N-hydroxybenzotriazole (3.0 g, 22.0 mmol), and N,N-diisopropylcarbodiimide (3.4 ml, 22.0 mmol). The suspension was shaken for 16 hours at room temperature. The resin was filtered off and washed with dichloro-methane/dimethyl formamide (3:2 v/v), dimethyl formamide, 2-propanol and dichloromethane (three times each). Unreacted oxime groups were capped by treating the resin with 80 ml of acetic anhydride/diisopropylethylamine/N-methylpyrrolidone (3:1:12 v/v/v) for 30 minutes at room temperature. The reaction mixture was removed by filtration and the resin was washed with N-methylpyrrolidone, 2-propanol/-dichloromethane (1:3 v/v) and dichloromethane (three times each). The resulting derivatized resin (4.96 g) was dried in vacuo.

Portions of 50 mg of this resin were transferred into 24 reactors of an organic synthesis robot. The resin was swollen by washing it with dichloromethane/dimethyl formamide (3:2 v/v) and dichloromethane (two times).

i) Deprotection of the Boc-group

The resin was pre-treated with 1 ml of 25% trifluoroacetic acid in dichloromethane and subsequently reacted under occasional nitrogen bubbling with 2 ml 25% trifluoroacetic acid for 30 minutes. The resin was washed with dichloromethane, 2-propanol, and dichloromethane (two times each).

ii) Coupling of first building block (A)

The resin was swollen by washing it with dichloromethane/dimethyl formamide (3:2 v/v). To the resin were added 1 ml of a 0.2 M solution of building block A (Boc-Pro-OH, Boc-(N-methyl)-Gly-OH, Boc-Gly-OH, or Boc-Phe-OH) in dichloromethane/ (3:2 v/v), 0.5 ml 0.44 M TBTU in dimethyl formamide, and 0.5 ml 0.44 M diisopropylethylamine in dichloromethane. The resin was incubated at room temperature for 60 minutes with occasional nitrogen bubbling. After removal of solvent, the resin was washed with dichloromethane/-dimethyl for-amide (3:2 v/v), dimethyl formamide, 2-propanol, and dichloromethane (two times each).

iii) Deprotection of the Boc-group

The Boc-group of building block A was removed using the procedure described in i).

iv) Coupling of second building block (B)

The second building block B was coupled using the same procedure as described in iii), using 0.2 M solutions of building block B (Boc-D-Cha-OH, or Boc-D-Phe-OH) in dichloromethane/dimethyl formamide (3:2 v/v).

v) Deprotection of the Boc-group

The Boc-group of building block B was removed using the procedure described in i), except for the pre-treatment step with trifluoroacetic acid.

vi) Coupling of the third building block (C)

The resin was washed with dichloromethane/dimethyl formamide (3:2 v/v) and, subsequently, washed twice with 2 ml of a 0.11 M solution of diisopropylethylamine in dichloromethane/dimethyl formamide (3:2 v/v). To the resin were added 1 ml of dichloromethane/dimethyl formamide (3:2 v/v), 0.5 ml of a 0.44 M solution of sulphonyl chlorides C (phenylsulphonyl chloride, 4-chlorophenylsulphonyl chloride, or 7-methoxynaphtylsulphonyl chloride) in dichloromethane/dimethyl formamide (3:2 v/v), and 0.5 ml of a 0.44 M solution of diisopropylethylamine in dichloromethane. The resin was reacted for 60 minutes at room temperature with occasional nitrogen bubbling. After removal of the reaction mixture, the resin was washed with dichloromethane/-dimethyl formamide (3:2 v/v), dimethyl formamide, 2-propanol, and dichloromethane (two times each).

vii) Cleavage of the product from the resin

The resin was washed twice with dimethyl formamide before the addition of 1.8 ml of a 0.2 M solution of guanidine.HCl in dimethyl formamide, and 0.2 ml of diisopropylethylamine. The resin was incubated at room temperature for 64 hours with occasional nitrogen bubbling. The resin was filtered off and the filtrate was collected in a glass tube. The resin was washed twice with dimethylformamide. The collected filtrates were evaporated to dryness.

Characterization

All compounds were characterized by reversed phase liquid chromatography on a Supelcosil LC-18-DB (4.6 mm×25 cm) column using following conditions: Flow: 1.0 ml/min; Buffers A: water, B: acetonitrile/water (9:1 v/v), C: 0.5M phosphate buffer pH=2.1; Gradient 1:0→30 min 55% A-25% B-20% C→15% A-65% B-20% C. UV-detection at 210 nm. Retention times are given in minutes in Table I.

Further, all compounds were analyzed by electrospray ionization mass spectrometry. Table I shows the M+H values detected in the positive mode. For all compounds the found mass is in agreement with the expected value.

TABLE I

Characterization (retention time of reversed phase HPLC and M + H peak in electrospray mass spectrometry) of acylguanidines prepared on Kaiser oxime resin.

| X: | phenyl-$SO_2$— | 4-chlorophenyl-$SO_2$— | 7-methoxynaphtyl-$SO_2$— |
|---|---|---|---|
| X-D-Cha-Pro-β-Ala-guanidine | r.t = 16.9 min<br>M + H = 521.4 | r.t = 20.1 min<br>M + H = 555.4 | r.t = 22.1 min<br>M + H = 601.4 |
| X-D-Phe-Pro-β-Ala-guanidine | r.t = 13.4 min<br>M + H = 515.4 | r.t = 17.0 min<br>M + H = 549.2 | r.t = 19.3 min<br>M + H = 595.4 |
| X-D-Cha-(N-methyl)-Gly-β-Ala-guanidine | r.t = 15.8 min<br>M + H = 495.4 | r.t = 18.9 min<br>M + H = 529.4 | r.t = 20.9 min<br>M + H = 575.4 |
| X-D-Phe-(N-methyl)-Gly-β-Ala-guanidine | r.t = 11.7 min<br>M + H = 489.2 | r.t = 15.5 min<br>M + H = 523.2 | r.t = 17.7 min<br>M + H = 569.4 |
| X-D-Cha-Gly-β-Ala-guanidine | r.t = 14.0 min<br>M + H = 481.2 | r.t = 17.2 min<br>M + H = 515.2 | r.t = 19.4 min<br>M + H = 561.4 |
| X-D-Phe-Gly-β-Ala-guanidine | r.t = 10.1 min<br>M + H = 475.2 | r.t = 14.1 min<br>M + H = 509.2 | r.t = 16.4 min<br>M + H = 555.4 |
| X-D-Cha-Phe-β-Ala-guanidine | r.t = 21.7 min<br>M + H = 571.4 | r.t = 24.2 min<br>M + H = 605.2 | r.t = 26.0 min<br>M + H = 651.4 |
| X-D-Phe-Phe-β-Ala-guanidine | r.t = 17.6 min<br>M + H = 565.4 | r.t = 20.8 min<br>M + H = 599.4 | r.t = 22.6 min<br>M + H = 645.4 |

Example 11

Further, the following compounds can be prepared by using the methods of the present invention HOOC-$CH_2$-D-Cha-(1-aminocyclohexylcarboxy)-β-Ala-guanidine;
(HOOC-$CH_2$)$_2$-D-Cha-Pro-β-Ala-guanidine;
HOOC-$CH_2$-N-Me-D-Cha-Pro-β-Ala-guanidine;
HOOC-$CH_2$-N-allyl-D-Cha-Pro-β-Ala-guanidine;
HOOC-$CH_2$-N-propargyl-D-Cha-Pro-β-Ala-guanidine;
HOOC-$CH_2$-N-benzyl-D-Cha-Pro-β-Ala-guanidine;
HOOC-$CH_2$-N-cyclopropyl-D-Cha-Pro-β-Ala-guanidine;
HOOC-$CH_2$-N-cyclobuty-D-Cha-Pro-β-Ala-guanidine;
HOOC-$CH_2$-N-cyclopentyl-D-Cha-Pro-β-Ala-guanidine;
HOOC-$CH_2$-N-cyclohexyl-D-Cha-Pro-β-Ala-guanidine;
2-propyl-pentanoyl-Asp(OMe)-Pro-β-Ala-guanidine;
2-propyl-pentanoyl-Asp-Pro-β-Ala-guanidine;
EthylS$O_2$-D-Cha-Pro-β-Ala-guanidine;
EthylS$O_2$-D-Phe-Pro-β-Ala-guanidine;
[2-(BzlS$O_2$-NH)-pyridinyl-1-$CH_2$-CO]-β-Ala-guanidine;
[3-(BzlS$O_2$-NH)-pyridin-2-one-1-$CH_2$-CO]-β-Ala-guanidine;
BzlS$O_2$-norLeu(cyclo)-Gly-β-Ala-guanidine;
N-Me-D-Phe-Pro-Glu(guanidine)-COOH;
N-Me-D-Phe-Pro-Glu(guanidine)-(2-oxazolyl);
N-Me-D-Cha-Pro-Glu(guanidine)-COOH;
N-Me-D-Cha-Pro-Glu(guanidine)-(2-thiazolyl);
N-Me-D-Cha-Pro-Glu(guanidine)-(2-oxazolyl);
HOOC-$CH_2$-D-Phe-Pro-Glu(guanidine)-COOH;
HOOC-$CH_2$-D-Phe-Pro-Glu(guanidine)-(2-thiazolyl);
HOOC-$CH_2$-D-Phe-Pro-Glu(guanidine)-(2-oxazolyl);
HOOC-$CH_2$-D-Cha-Pro-Glu(guanidine)-COOH;
HOOC-$CH_2$-D-Cha-Pro-Glu(guanidine)-(2-oxazolyl);
EthylS$O_2$-D-Phe-Pro-Glu(guanidine)-COOH;
EthylS$O_2$-D-Phe-Pro-Glu(guanidine)-(2-thiazolyl);
EthylS$O_2$-D-Phe-Pro-Glu(guanidine)-(2-oxazolyl);

EthylSO$_2$-D-Cha-Pro-Glu(guanidine)-COOH;
EthylSO$_2$-D-Cha-Pro-Glu(guanidine)-(2-oxazolyl);
1-Piq-Pro-Glu(guanidine)-COOH;
1-Piq-Pro-Glu(guanidine)-(2-oxazolyl);
HOOC-CH$_2$-D-Cha-(N-cyclopentyl)-Gly-Glu(guanidine)-(2-thiazolyl);
N-Me-D-Phe-(N-cyclopentyl)-Gly-Glu(guanidine)-(2-thiazolyl);
2-propyl-pentanoyl-Asp(OMe)-Pro-Glu(guanidine)-(2-thiazolyl);
2-hydroxy-3-cyclohexyl-propionyl-Pro-Glu(guanidine)-(2-thiazolyl);
1-Piq-(N-cyclopentyl)-Gly-Glu(guanidine)-(2-thiazolyl);
Diphenylpropionyl-Pro-Glu(guanidine)-(2-thiazolyl);
the compounds wherein the residue:

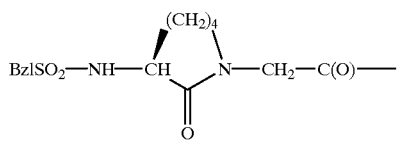

is coupled to -Glu(guanidine)—COOH, -Glu(guanidine)-(2-thiazolyl) or
Glu(guanidine)-(2-oxazolyl);
9-hydroxy-fluorene-9-carboxyl-Pro-β-Ala-guanidine;
9-hydroxy-fluorene-9-carboxyl-(N-cyclopentyl)Gly-β-Ala-guanidine;
9-hydroxy-fluorene-9-carboxyl-azetidine-2-carboxyl-β-Ala-guanidine.

Example 12
Anti-Thrombin Assay

Thrombin (Factor IIa) is a factor in the coagulation cascade.

The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the IC$_{50}$-value of a test compound.

Test Medium

Tromethamine-NaCl-polyethylene glycol 6000 (TNP) buffer. Reference compound: I2581 (Kabi) Vehicle: TNP buffer. Solubilisation can be assisted with dimethylsulphoxide, methanol, ethanol, acetonitrile or tert.-butyl alcohol which are without adverse effects in concentrations up to 2.5% in the final reaction mixture.

Technique

Reagent*: 1. Tromethamine-NaCl (TN) buffer. Composition of the buffer: Tromethamine (Tris) 6.057 g (50 mmol), NaCl 5.844 g (100 mmol), water to 1 l. The pH of the solution is adjusted to 7.4 at 37° C. with HCl (10 mmol.l$^{-1}$). 2. TNP buffer: Polyethylene glycol 6000 is dissolved in TN buffer to give a concentration of 3 g.l$^{-1}$. 3. S-2238 solution: One vial S-2238 (25 mg; Kabi Diagnostica, Sweden) is dissolved in 20 ml TN buffer to give a concentration of 1.25 mg.ml$^{-1}$ (2 mmol.l$^{-1}$). 4. Thrombin solution: Human thrombin (16 000 nKat.vial$^{-1}$; Centraal Laboratorium voor Bloedtransfusie, Amsterdam, The Netherlands) is dissolved in TNP buffer to give a stock solution of 835 nKat.ml$^{-1}$. Immediately before use this solution is diluted with TNP buffer to give a concentration of 3.34 nKat.ml$^{-1}$.

All ingredients used are of analytical grade

For aqueous solutions ultrapure water (Milli-Q quality) is used.

Preparation of Test and Reference Compound Solutions

The test and reference compounds are dissolved in Milli-Q water to give stock concentrations of $10^{-2}$ mol.l$^{-1}$. Each concentration is stepwise diluted with the vehicle to give concentrations of $10^{-3}$, $10^{-4}$ and $10^{-5}$ mol.l$^{-1}$. The dilutions, including the stock solution, are used in the assay (final concentrations in the reaction mixture: $3.10^{-3}$; $10^{-3}$; $3.10^{-4}$; $10^{-4}$; $3.10^{-5}$; $10^{-5}$; $3.10^{-6}$ and $10^{-6}$ mol.l$^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).

All data are collected in an IBM personal computer using LOTUS-MEASURE. For each compound concentration (expressed in mol.l$^{-1}$ reaction mixture) and for the blank the absorbance is plotted versus the reaction time in min.

Evaluation of Responses

For each final concentration the maximum absorbance was calculated from the assay plot. The IC$_{50}$-value (final concentration, expressed in μmol.l$^{-1}$, causing 50% inhibition of the maximum absorbance of the blank) was calculated using the logit transformation analysis according to Hafner et al. (Arzneim.-Forsch./Drug Res. 1977; 27(II): 1871–3).

In the following table, IC$_{50}$-values of compounds of the invention are listed:

| Example | IC$_{50}$-value (μM) |
| --- | --- |
| 1 | 0.24 |
| 2 | 0.034 |
| 4 | 2.59 |
| 6 | 0.32 |

We claim:
1. A compound having the formula I

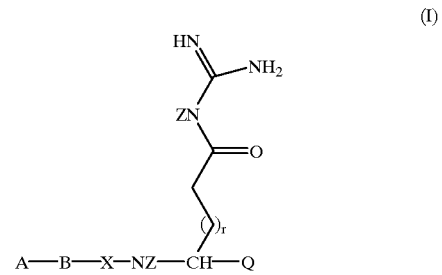

wherein
A is H, optionally substituted D,L α-hydroxyacetyl, R$^1$, R$^1$—O—C(O)—, R$^1$—C(O)—, R$^1$—SO$_2$—, R$^2$OOC—(CHR$^2$)$_m$—SO$_2$—, R$^2$OOC-(CHR$^2$)$_m$—, H$_2$NCO-(CHR$^2$)$_m$—, or an N-protecting group, wherein $R^1$ is selected from (1–12C)alkyl, (2–12C)alkenyl, (2–12C)alkynyl and (3–8C)cycloalkyl, which groups may optionally be substituted with (3–8C)cycloalkyl, (1–6C)alkoxy, oxo, OH, COOH, $CF_3$ or halogen, and from (6–14C)aryl, (7–15C)aralkyl and (8–16)aralkenyl, the aryl groups of which may optionally be substituted with (1–6C)alkyl, (3–8C)cycloalkyl, (1–6C)alkoxy, OH, COOH, $CF_3$ or halogen; each group $R^2$ is independently H or has the same meaning as $R^1$; m is 1, 2 or 3;

B is a bond, an amino acid of the formula —NH—CH[$(CH_2)_p$C(O)OH]—C(O)— or an ester derivative thereof with p being 0, 1, 2 or 3, —N((1–12C)alkyl)—$CH_2$—CO—, —N((2–12C)alkenyl)—$CH_2$—CO—, —N((2–12C)alkynyl)—$CH_2$—CO—, —N(benzyl)—$CH_2$—CO—, D-1-Tiq, D-3-Tiq, D-Atc, Aic, D-1-Piq, D-3-Piq or a L- or D-amino acid having a hydrophobic, basic or neutral side chain, which amino acid may optionally be N-(1–6C)alkyl substituted; or A and B together are the residue $R^3R^4N$—$CHR^5$—C(O)—, wherein $R^3$ and $R^4$ independently are $R^1$, $R^1$—O—C(O)—, $R^1$—C(O)—, $R^1$—$SO_2$—, $R^2OOC$—$(CHR^2)_m$—$SO_2$—, $R^2OOC$—$(CHR^2)_m$—, $H_2NCO$—$(CHR^2)_m$—, or an N-protecting group, or one of $R^3$ and $R^4$ is connected with $R^5$ to form a 5- or 6-membered ring together with "N–C" to which they are bound, which ring may be fused with an aliphatic or aromatic 6-membered ring; and $R^5$ is a hydrophobic, basic or neutral side chain;

X is an L-amino acid with a hydrophobic side chain, being a (1–12C)alkyl, optionally substituted with one or more (3–8C)cycloalkyl groups or (6–14C)aryl groups, which hydrophobic side chain may optionally be substituted with halogen, trifluoromethyl, lower alkyl, lower alkoxy, phenyloxy, or benzyloxy, or X is serine, threonine, a cyclic amino acid optionally containing an additional heteroatom selected from N, O and S, and optionally substituted with (1–6C)alkyl, (1–6C)alkoxy, benzyloxy or oxo, or X is —$NR^2$—$CH_2$—C(O)— or the fragment

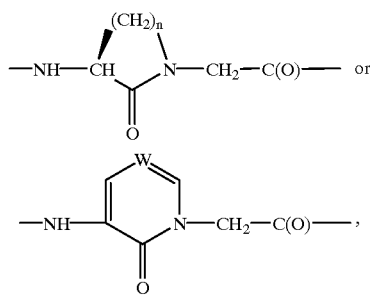

wherein n is 2, 3, or 4, and W is CH or N;

Q is H or —C(O)Y, wherein Y is H, —$CHF_2$, —$CF_3$, —CO—NH—(1–6C)alkylene-$C_6H_5$, —$COOR^6$ and $R^6$ being H or (1–6C)alkyl, —$CONR^7R^8$ and $R^7$ and $R^8$ being independently H or (1–6C)alkyl or $R^7$ and $R^8$ together being (3–6C)alkylene, or Y is a heterocycle selected from 2-thiazole, 2-thiazoline, 2-benzothiazole, 2-oxazole, 2-oxazoline and 2-benzoxazole, which heterocycles may optionally be substituted with (1–6C)alkyl, (1–6C)alkoxy or oxo;

Z is H or (1–6C)alkyl;

r is 0 or 1 if Q is —C(O)Y or is 0, 1, 2, 3 or 4 if Q is H; or a prodrug thereof or a pharmaceutically acceptable salt thereof.

2. The compound of claim 1, wherein X is an L-amino acid with a hydrophobic side chain, serine, threonine or —$NR^2$—$CH_2$—C(O)—; and Z is H or methyl.

3. The compound of claim 1, wherein A is as previously defined; B is a bond, an amino acid of the formula —NH—CH[$(CH_2)_p$C(O)OH]—C(O)— or an ester derivative thereof with p being 0, 1, 2 or 3, —N((1–6C)alkyl)—$CH_2$—CO—, —N((2–6C)alkenyl)—$CH_2$CO—, —N(benzyl)—$CH_2$—CO—, D-1-Tiq, D-3-Tiq, D-Atc, Aic, D-1-Piq, D-3-Piq or a D-amino acid having a hydrophobic side chain, which amino acid may optionally be N-(1–6C)alkyl substituted;

or A and B together are the residue $R^3R^4N$—$CHR^5$—C(O)—; and X is a cyclic amino acid optionally containing an additional heteroatom selected from N, O and S, and optionally substituted with (1–6C)alkyl, (1–6C)alkoxy, benzyloxy or oxo, or X is —$NR^2$—$CH_2$—C(O)— or the fragment

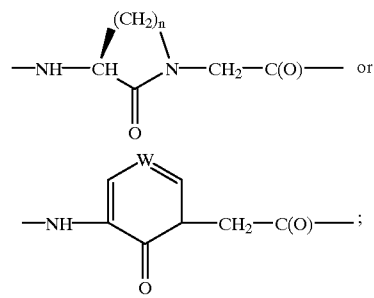

and Z is H or methyl.

4. The compound of claim 3, wherein A is H, 2-hydroxy-3-cyclohexyl-propionyl-, 9-hydroxy-fluorene-9-carboxyl, $R^1$, $R^1$—$SO_2$—, $R^2OOC$—$(CHR^2)_m$—$SO_2$—, $R^2OOC$—$(CHR^2)_m$—, $H_2NCO$—$(CHR^2)_m$—, or an N-protecting group, wherein $R^1$ is selected from (1–12C)alkyl, (2–12C)alkenyl, (6–14C)aryl, (7–15C)aralkyl and (8–16)aralkenyl; each group $R^2$ is independently H or has the same meaning as $R^1$;

B is a bond, D-1-Tiq, D-3-Tiq, D-Atc, Aic, D-1-Piq, D-3-Piq or a D-amino acid having a hydrophobic side chain, which amino acid may optionally be N-(1–6C) alkyl substituted;

or A and B together are the residue $R^3R^4N$—$CHR^5$—C(O)—;

Y is —CO—NH—(1–6C)alkylene-$C_6H_5$, —$COOR^6$, —$CONR^7R^8$, or Y is a heterocycle selected from 2-thiazole, 2-thiazoline, 2-benzothiazole, 2-oxazole, 2-oxazoline and 2-benzoxazole.

5. The compound of claim 4, wherein A is $R^1$—$SO_2$—, $R^2OOC$—$(CHR^2)_m$—;

B is a bond, D-1-Tiq, D-3-Tiq, D-Atc, Aic, D-1-Piq, D-3-Piq or a D-amino acid having a hydrophobic side chain;

or A and B together are the residue $R^3R^4N$—$CHR^5$—C(O)—, wherein at least one of $R^3$ and $R^4$ is $R^2OOC$—$(CHR^2)_m$— or $R^1$—$SO_2$— and the other independently is (1–12C)alkyl, (2–12C)alkenyl, (2–12C)alkynyl, (3–8C)cycloalkyl, (7–15C)aralkyl, $R^1$—$SO_2$— or $R^2OOC$—$(CHR^2)_m$—, and $R^5$ is a hydrophobic side chain;

Y is —CO—NH—(1–6C)alkylene-$C_6H_5$, —$COOR^6$ and $R^6$ being H or (1–3C)alkyl, —$CONR^7R^8$, $R^7$ and $R^8$ being independently H or (1–3C)alkyl or $R^7$ and $R^8$ together being (3–5C)alkylene, or Y is a heterocycle selected from 2-thiazole, 2-benzothiazole, 2-oxazole or 2-benzoxazole.

6. The compound of claim 5, wherein A is $R^2OOC—(CHR^2)_m—$;

B is a D-amino acid having a hydrophobic side chain;

or A and B together are the residue $R^3R^4N—CHR^5—C(O)—$, wherein at least one of $R^3$ and $R^4$ is $R^2OOC—(CHR^2)_m—$ and the other independently is (1–12C)alkyl, (3–8C)cycloalkyl, $R^1—SO_2—$ or $R^2OOC—(CHR^2)_m—$;

and X is 2-azetidine carboxylic acid, proline, pipecolic acid, 4-thiazolidine carboxylic acid, 3,4-dehydro-proline, or 2-octahydroindole carboxylic acid.

7. The compound of claim 6, wherein A is $HOOC—CH_2—$;

B is D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, or D-Chg;

or A and B together are the residue $R^3R4N—CHR^5—C(O)—$, wherein at least one of $R^3$ and $R^4$ is $HOOC—CH_2—$ and the other independently is methyl, (1–4C)alkyl-$SO_2$ or $HOOC—CH_2—$ and $R^5$ is (3–8C)cycloalkyl, (3–8C)cycloalkyl(1–4C)alkyl, phenyl, or benzyl, each of which are optionally substituted with chlorine or with (1–4C)alkoxy.

8. The compound of claim 5, wherein A is $R^1—SO_2—$;

B is a bond, D-1-Tiq, D-3-Tiq, D-Atc, Aic, D-1-Piq, D-3-Piq or a D-amino acid having a hydrophobic side chain;

or A and B together are the residue $R^3R^4N-CHR^5—C(O)—$, wherein at least one of $R^3$ and $R^4$ is $R^1—SO_2—$ and the other independently is (1–12C)alkyl or $R^1—SO_2—$;

X is 2-azetidine carboxylic acid, proline, pipecolic acid, 4-thiazolidine carboxylic acid, 3,4-dehydro-proline, 2-octahydroindole carboxylic acid, or the fragment

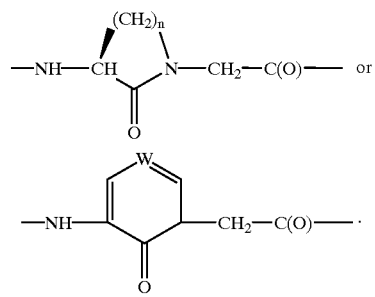

9. The compound of claim 8, wherein A is Ethyl—$SO_2$— or Benzyl—$SO_2$—;

B is a bond, D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, or D-Chg; or A and B together are the residue $R^3R^4N—CHR^5—C(O)—$, wherein at least one of $R^3$ and $R^4$ is Ethyl—$SO_2$— or Benzyl—$SO_2$— and the other independently is (1–12C)alkyl or $R^1—SO_2—$ and $R^5$ is (3–8C)cycloalkyl, (3–8C)cycloalkyl(1–4C)alkyl, phenyl, benzyl, or diphenylmethinyl, which groups are optionally substituted with chlorine or (1–4C)alkoxy.

10. The compound of claim 5, wherein Q is H and r is 0, 1 or 2.

11. A pharmaceutical composition comprising the compound of claim 1 and pharmaceutically suitable auxiliaries.

12. A method for treating or preventing thrombin-mediated and thrombin-associated diseases, comprising administering to a patient in need thereof a thrombin-inhibiting effective amount of a compound according to claim 1.

13. A process for making a pharmaceutical preparation, comprising admixing a compound according to claim 1 with pharmaceutically acceptable auxiliaries.

* * * * *